US012514953B2

(12) United States Patent
Husmark et al.

(10) Patent No.: US 12,514,953 B2
(45) Date of Patent: Jan. 6, 2026

(54) ABSORBENT UNDERGARMENT HAVING ANTI-ODOR AND SKIN-BENEFICIAL EFFECTS

(71) Applicant: Essity Hygiene and Health Aktiebolag, Gothenburg (SE)

(72) Inventors: Ulrika Husmark, Gothenburg (SE); Frida Ryttsén, Gothenburg (SE)

(73) Assignee: ESSITY HYGIENE AND HEALTH AKTIEBOLAG, Göteborg (CH)

( * ) Notice: Subject to any disclaimer, the term of this patent is extended or adjusted under 35 U.S.C. 154(b) by 622 days.

(21) Appl. No.: 17/792,164

(22) PCT Filed: Feb. 10, 2021

(86) PCT No.: PCT/EP2021/053118
§ 371 (c)(1),
(2) Date: Jul. 12, 2022

(87) PCT Pub. No.: WO2021/160627
PCT Pub. Date: Aug. 19, 2021

(65) Prior Publication Data
US 2023/0051090 A1 Feb. 16, 2023

(30) Foreign Application Priority Data
Feb. 11, 2020 (WO) ................. PCT/SE2020/050141

(51) Int. Cl.
*A61L 15/40* (2006.01)
*A61F 13/496* (2006.01)
*A61L 15/46* (2006.01)

(52) U.S. Cl.
CPC ............ *A61L 15/40* (2013.01); *A61F 13/496* (2013.01); *A61L 15/46* (2013.01)

(58) Field of Classification Search
CPC ........ A61F 13/15; A61F 13/53; A61F 13/496; A61F 13/51121; A61L 15/40; A61L 15/46; A61L 12/42
See application file for complete search history.

(56) References Cited

U.S. PATENT DOCUMENTS 3,860,003 A * 1/1975 Buell ................ A61F 13/49017 604/385.25
5,137,537 A * 8/1992 Herron ..................... D04H 1/64 8/129

(Continued)

FOREIGN PATENT DOCUMENTS

CA 2029014 * 3/1997 .............. B01J 20/24
CN 1769560 A 5/2006

(Continued)

OTHER PUBLICATIONS

International Preliminary Report on Patentability (PCT/IPEA/409) issued in corresponding International Patent Application No. PCT/EP2021/053118 dated Apr. 19, 2022. (54 pages).

(Continued)

*Primary Examiner* — Michele Kidwell
(74) *Attorney, Agent, or Firm* — BUCHANAN INGERSOLL & ROONEY PC

(57) ABSTRACT

The disclosure relates to an absorbent undergarment comprising a fabric layer defining a waist opening, two leg openings and a crotch region between the leg openings, the absorbent undergarment further comprising an absorbent pad covering at least part of said crotch region and being permanently attached to the fabric layer. The absorbent pad comprises at least one absorbent layer and a skin-facing layer. At least one layer, selected from said absorbent layer, said skin-facing layer or an optionally present wicking layer, comprises naturally-derived fibers comprising a polycarboxylic acid. The polycarboxylic acid has at least one carboxyl (Continued)

group covalently bound to the naturally-derived fibers and at least one free carboxyl group.

21 Claims, 3 Drawing Sheets

(56) References Cited

U.S. PATENT DOCUMENTS

| | | | | | |
|---|---|---|---|---|---|
| 5,447,977 | A * | 9/1995 | Hansen | A61L 15/60 | 523/205 |
| 5,800,418 | A * | 9/1998 | Ahr | A61F 13/53 | 604/374 |
| 6,471,824 | B1 * | 10/2002 | Jewell | D06M 13/192 | 162/146 |
| 2005/0072542 | A1 * | 4/2005 | Sears | D21C 9/002 | 162/158 |
| 2006/0019571 | A1 | 1/2006 | Lange et al. | | |
| 2008/0114327 | A1 | 5/2008 | Barge | | |
| 2009/0238811 | A1 * | 9/2009 | McDaniel | A61L 2/00 | 424/94.2 |
| 2014/0039432 | A1 | 2/2014 | Dunbar et al. | | |
| 2017/0021051 | A1 | 1/2017 | Richards et al. | | |
| 2017/0056253 | A1 * | 3/2017 | Chester | A61F 13/51478 | |

FOREIGN PATENT DOCUMENTS

| | | | |
|---|---|---|---|
| CN | 108135760 | A | 6/2018 |
| EP | 2879534 | B1 | 3/2017 |
| EP | 3187047 | A1 | 7/2017 |
| EP | 3046592 | B1 | 9/2018 |
| JP | 2013112903 | A | 6/2013 |
| JP | 2016079530 | A | 5/2016 |
| WO | 2007013967 | A2 | 2/2007 |
| WO | 2014176677 | A1 | 11/2014 |

OTHER PUBLICATIONS

International Search Report (PCT/ISA/210) and Written Opinion (PCT/ISA/237) mailed on May 19, 2021, by the European Patent Office as the International Searching Authority for International Application No. PCT/EP2021/053118. (11 pages).

Written Opinion of the International Preliminary Examining Authority (PCT/IPEA/408) issued in corresponding International Patent Application No. PCT/EP2021/053118 dated Jan. 19, 2022. (7 pages).

Office Action issued on Oct. 18, 2024, by the Colombia Patent Office in corresponding Colombia Patent Application No. NC2022/0011166, and a partial English Translation of the Office Action. (12 pages).

B. Li et al., "Preparation and catalytic performance of Fe(III)-citric acid modified cotton fiber complex as a novel cellulose fiber-supported heterogeneous photo-Fenton catalyst", Cellulose, 2015, vol. 22, pp. 1295-1309; https://link.springer.com/article/10.1007/s10570-015-0562-x.

Vukusic et al.; "Cotton textiles modified with citric acid as efficient anti-bacterial agent for prevention of nosocomial infections". Croat Med J., Basic Science, Feb. 2011, vol. 52, No. 1, pp. 68-75; https://www.ncbi.nlm.nih.gov/pmc/articles/PMC3046493/.

Office Action (Communication pursuant to Article 94(3) EPC) issued on Feb. 21, 2024, in corresponding European Patent Application No. 21705135.8. (8 pages).

Office Action issued on May 26, 2025, by the Colombian Patent Office in corresponding Colombian Patent Application No. NC2022/0011166, and an English Translation of the Office Action. (20 pages).

* cited by examiner

ABSORBENT UNDERGARMENT HAVING ANTI-ODOR AND SKIN-BENEFICIAL EFFECTS

TECHNICAL FIELD

The present disclosure relates to an absorbent undergarment for the purpose of absorbing body fluids such as urine and menstrual fluid.

The present disclosure further relates to a method for the manufacture of an absorbent undergarment of the above-mentioned type.

BACKGROUND

Absorbent undergarments are worn against the skin or near the crotch region for the purpose of absorbing body fluids such as urine and menstrual fluid. Conventionally, such absorbent undergarments comprise a fabric layer and an absorbent pad having absorbent properties.

However, the entrapment of body liquids in the absorbent pad of the absorbent undergarment may result in unwanted side-effects such as microbial growth, odors and disturbance of the natural skin pH. These factors may in turn cause different forms of skin irritation and primary or secondary skin infections. For example, an increase in skin pH may result in an increased activity of enzymes such as lipases and proteases. Further, the development of odors causes discomfort and is a source of embarrassment for the user.

The use of silver antimicrobial fibers in absorbent undergarments to control odor and microbial growth has been previously known in the art by, for example international patent application PCT/CA2014/000389. However, silver is of limited supply and the methods for obtaining and processing silver has a negative environmental impact.

Thus, there is still a need in the art for improved absorbent undergarments having anti-odor and skin-beneficial effects.

SUMMARY

The present inventors have found that by providing an absorbent undergarment according to claim 1 and a method according to claim 14, the above objectives are at least partially met.

Therefore, according to one aspect, the present invention relates to an absorbent undergarment comprising a fabric layer defining a waist opening, two leg openings and a crotch region between the leg openings. The absorbent undergarment further comprises an absorbent pad covering at least part of the crotch region and is permanently attached to the fabric layer. The absorbent pad comprises at least one absorbent layer and a skin-facing layer, wherein at least one layer, selected from the absorbent layer, the skin-facing layer or an optionally present wicking layer, comprises naturally-derived fibers. Further, the naturally-derived fibers comprise a polycarboxylic acid. The polycarboxylic acid has at least one carboxyl group which reacts with the free hydroxyl group of the naturally-derived fibers to form a covalent bond. The polycarboxylic acid has at least one additional free carboxyl group that is not bonded to the naturally-derived fibers. The free carboxyl group confers a low pH to the treated layer resulting in anti-microbial effects that remain present after laundering of the absorbent undergarment. Further, the polycarboxylic acid is a natural and sustainable additive.

The polycarboxylic acid may have between two to ten carboxyl groups. A first carboxyl group is required to allow binding of the polycarboxylic acid to the material constituting the absorbent undergarment, whereas the additional carboxyl groups (two to ten) provide the acidic properties. Preferably, the polycarboxylic acid has three to five carboxyl group, and most preferably three carboxyl groups.

The polycarboxylic acid may have 2 to 12 carbon atoms in a main chain, e.g., 4 to 6 carbon atoms in a main chain, wherein the polycarboxylic acid is preferably selected from the group consisting of citric acid, isocitric acid, citraconic acid, tartaric acid, itaconic acid, 1,2,3-propanetricarboxylic acid, 1,2,3,4-butanetetracarboxylic acid, glutaric acid, alpha-ketoglutaric acid, malic acid, malonic acid, 2-hydroxymalonic acid, oxalic acid, oxalosuccinic acid, succinic acid, carboxy succinic acid, 1,2 dimethylsuccinic acid, adipic acid, pimelic acid, 2-methyl tricarballylic acid, aconitic acid, 1,2,4-butane tricarboxylic acid, polymers of acrylic acid, and mixtures thereof, wherein the acid is preferably citric acid. Use of succinic acid, citric acid, and α-ketoglutaric acid as an additive has been shown to be safe in use in the food industry. Further, the carboxylgroups in citric acid are in close vicinity to each other.

The at least one carboxyl group in the polycarboxylic acid may be covalently bound to the naturally-derived fibers by forming an ester bond with a hydroxyl group present in the naturally-derived fibers. An ester bond is a covalent bond thus allowing the polycarboxylic acid to chemically bond to the fibers in the material of the absorbent undergarment.

The selected layer may comprise between 20% to 100% naturally-derived fibers, alternatively between 40% and 100% naturally-derived fibers or between 60% and 100% naturally-derived fibers.

The naturally-derived fibers may be selected from the group consisting of natural fibers and man-made regenerated fibers from a natural source. No chemical processes are required for the production of natural fibers. On the other hand, the manufacturing process of man-made regenerated fibers is such that it allows for the modification of the structure and properties of the man-made regenerated fibers.

The naturally-derived fibers may be selected from the group consisting of cotton, wool, silk, cellulose, regenerated cellulose, rayon, viscose, modal, lyocell, tencel, bamboo, hemp, flax, ramie, coir or banana. The naturally-derived may be selected from the group consisting of cotton or viscose fibers. The production of cotton fibers does not involve the (partial) degradation of cellulose. However, the cost of manufacturing is generally lower for viscose fibers.

The polycarboxylic acid in the present disclosure may be bound to naturally-derived fibers through an ester bond. An ester bond is a covalent bond thus allowing the polycarboxylic acid to chemically bond to the fibers in the material of the absorbent undergarment. A catalyst may be used to accelerate the esterification reaction. The catalyst may be selected from the group consisting of sodium hypophosphite, disodium monohydrogen phosphate, sodium dihydrogen phosphate, sodium salt and maleic acid or sodium pyrophosphate. Further, a curing step may be included.

The selected layer comprising the polycarboxylic acid according to the present disclosure, may be substantially free of petroleum-based materials. Petroleum is a non-renewable resource and the supply thereof is therefore limited.

The treated layer comprising the acidic solution according to the present disclosure may have a pH after washing of from 2.5 to 6.5 when measured according to the method described herein. The low pH inhibits microbial growth within the absorbent undergarment and contributes to an acidic environment between the absorbent undergarment and the skin in the crotch region. Studies have shown that natural skin surface pH is on average below 5, which is beneficial for its resident flora, see e.g. Lambers H et al (2006), *Int J Cosmet Sci,* 28 (5), 359-70.

The present disclosure further pertains to a method for manufacturing an absorbent undergarment as defined in this disclosure, comprising a step of treating naturally-derived fibers with a treatment solution comprising one or more polycarboxylic acid, or optionally a mixture of one or more polycarboxylic acids with salts thereof. The polycarboxylic acid may have two to ten carboxyl groups, preferably three to five carboxyl groups, and more preferably three carboxyl groups. The polycarboxylic acid may have 2 to 12 carbon atoms in a main chain, e.g., 4 to 6 carbon atoms in a main chain, wherein the compound is preferably selected from the group consisting of citric acid, isocitric acid, citraconic acid, tartaric acid, itaconic acid, 1,2,3-propanetricarboxylic acid, 1,2,3,4-butanetetracarboxylic acid, glutaric acid, alpha-ketoglutaric acid, malic acid, malonic acid, 2-hydroxymalonic acid, oxalic acid, oxalosuccinic acid, succinic acid, carboxy succinic acid, 1,2 dimethylsuccinic acid, adipic acid, pimelic acid, 2-methyl tricarballylic acid, aconitic acid, 1,2,4-butane tricarboxylic acid, polymers of acrylic acid, and mixtures thereof, wherein the acid is preferably citric acid. Optionally, the absorbent undergarment is dried after the treatment step. Finally, the absorbent garment is cured.

At least one, preferably all, of the following conditions is fulfilled during manufacturing of the absorbent underwear:

(i) the concentration of the polycarboxylic acid in the treatment solution is 2 to 80 wt.-%, preferably 2.5 to 50 wt.-% and more preferably 10 to 20% wt.-% based on the total weight of the treatment solution, (ii) the treatment time is 20 sec to 30 min, preferably 30 sec to 15 min, in particular 30 sec to 5 min, (iii) the curing time is 10 sec to 10 min, preferably 10 sec to 1 min, in particular 10 sec to 30 sec, (iv) the curing temperature is 100° C. to 200° C., preferably 110° C. to 180° C., more preferably 140° C. to 170° C.

The treatment solution may comprise a catalyst. The catalyst may be selected from the group consisting of sodium hypophosphite, disodium monohydrogen phosphate, sodium dihydrogen phosphate, sodium salt of maleic acid or sodium pyrophosphate.

The selected layer of the absorbent undergarment according to the present disclosure may have a pH after one washing cycle of from 2.5 to 6.5, preferably from 4.6 to 5.7, more preferably from 4.6 to 5.2, when measured according to the method described herein. The selected layer of the absorbent undergarment according to the present disclosure may have a pH after 5 washing cycles of from 2.5 to 6.5 when measured according to the method described herein.

BRIEF DESCRIPTION OF THE FIGURES

The present disclosure will be further explained hereinafter by means of examples and with reference to the appended drawings wherein.

DETAILED DESCRIPTION

Figure 1:
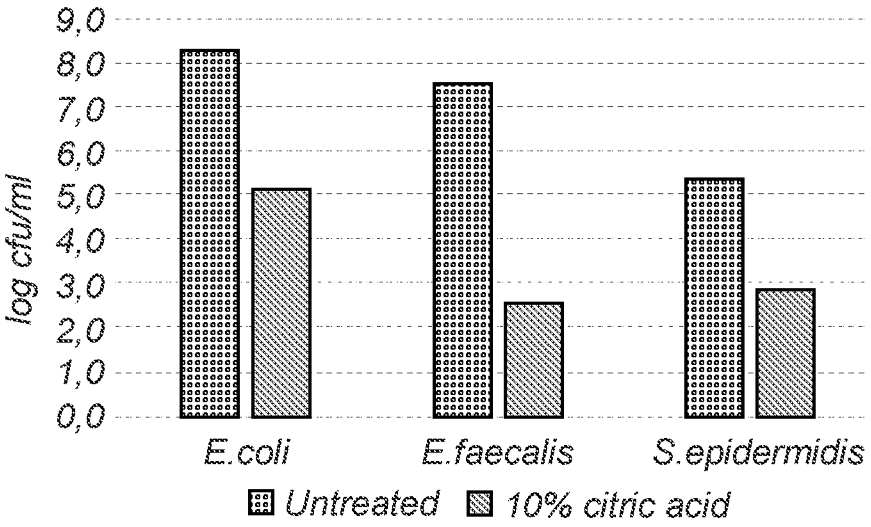
FIG. 1 shows a graph depicting bacterial growth on cotton fabric.

The present disclosure relates to an absorbent undergarment comprising a fabric layer defining a waist opening, two leg openings and a crotch region between the leg opening. The absorbent undergarment further comprises an absorbent pad covering at least part of the crotch region and is permanently attached to the fabric layer. The absorbent pad comprises at least one absorbent layer and a skin-facing layer. Optionally, the absorbent pad may comprise a wicking layer.

In the absorbent undergarment, at least one layer selected from said skin-facing layer or said at least one absorbent layer, and/or an optionally present wicking layer comprises naturally-derived fibers comprising a polycarboxylic acid. The polycarboxylic acid may have between two to ten carboxyl groups, preferably three to five and more preferably three carboxyl groups. The carboxyl groups may be attached to the fibers by an esterification process forming an ester bonding between the polycarboxylic acid and the hydroxylgroup of the fibers.

As used herein, the term "naturally-derived fibers" refers to fibers derived from a natural source. Naturally-derived fibers include natural fibers which may be plant-based such as cotton; or animal-based such as wool or silk. Naturally-derived fibers further include man-made regenerated fibers from a natural source such as regenerated cellulose, rayon, viscose, modal, lyocell, tencel, bamboo, hemp, flax, ramie, coir and banana. Synthetic man-made fibers such as nylon, acrylic, polyester or elastane, are not considered to be naturally-derived fibers according to the present disclosure.

As used herein, the term "absorbent undergarment" refers to garments that are worn and intended to be placed against the skin of the wearer to absorb and contain body exudates, such as urine and menstrual fluid. The undergarment according to the present disclosure is intended to be laundered or otherwise restored after use for reuse as a sanitary article.

By "laundering" it is meant that the absorbent undergarment can be cleaned by laundering. The absorbent undergarment may thus be subjected to an aqueous solution containing detergent without losing its structural features. This aqueous solution may be heated as part of the laundering process, e.g. to 30° C. or 60° C.

The term "fabric" as used in the present disclosure may refer to a single or multiple layers of fabrics. The fabric may be knitted or woven.

By "permanently attached", it is meant that the absorbent pad is not intended to separate from the fabric layer before, during, or after use. The absorbent pad is not necessarily directly bonded to the fabric layer, but instead may be attached via the leg opening seams.

As used herein, the term "acidic solution" refers to a solution having an acid pH, i.e. less than pH 7.

In all figures in the following detailed description, the same reference numerals will be used to indicate the same elements.

Figure 3:
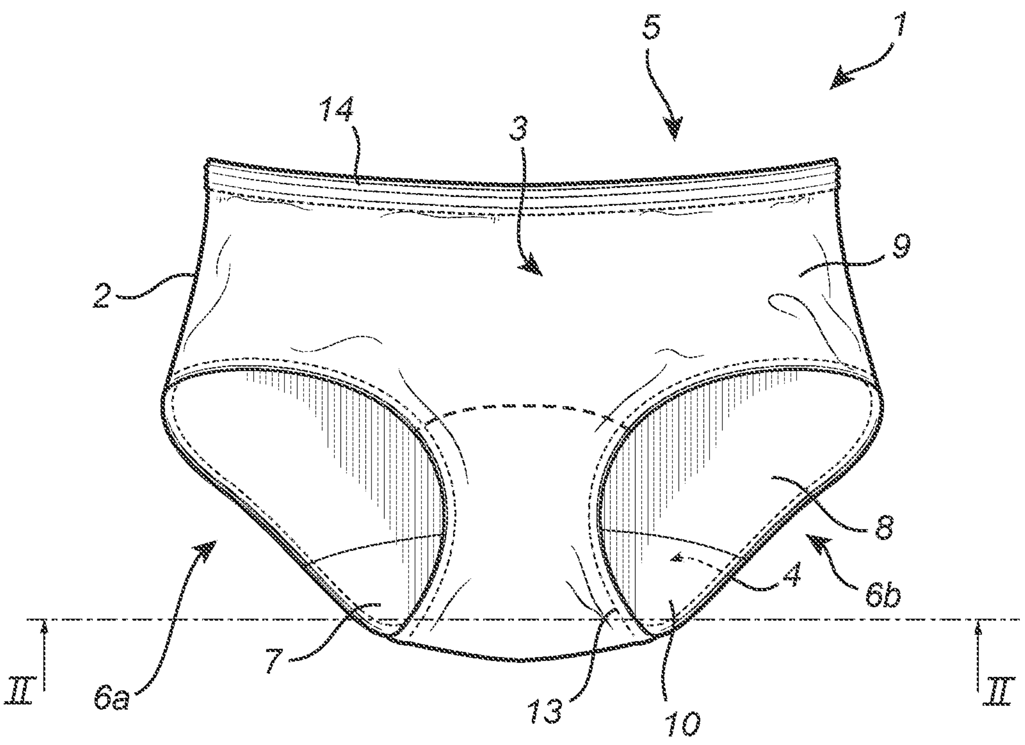
FIG. 3 shows a front view of the absorbent undergarment.

FIG. 3 is a front view of the absorbent undergarment according to the present disclosure. The absorbent undergarment 1 comprises a fabric layer 2 having a front side 3, a back side 4 and a waist opening 5. The fabric layer 2 has two leg openings 6*a* and 6*b*, and a crotch region 7 in between the leg openings 6*a* and 6*b*. The fabric layer 2 further includes an interior surface 8 (i.e., a surface of the fabric layer 2 that wholly or partially contacts the body of the wearer) and an exterior surface 9 (i.e. a surface of the fabric layer 2 that does not contact the body of the wearer). The absorbent undergarment 1 further comprises an absorbent pad 10 covering at least part of said crotch region. In FIG. 3, a leg opening seam 13 lines the leg openings 6*a* and 6*b*. The leg opening seam 13 may be provided by conventional stitching or gluing techniques. The leg opening seam may comprise an elastic member such as elastic bonding film. Further, the leg opening seam may serve to bond the skin-facing layer, the absorbent pad, the outer layer and the optionally present wicking layer together. The absorbent undergarment 1 may further comprise a waist band 14.

Figure 4:
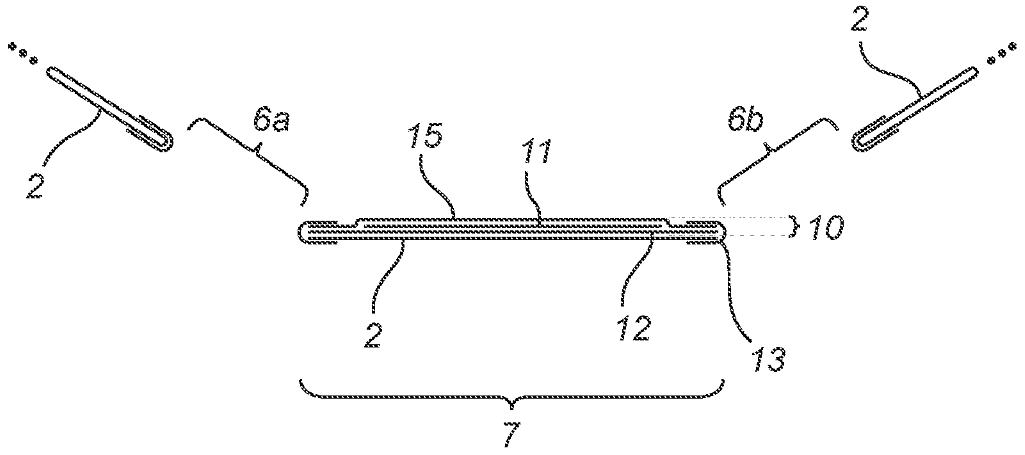
FIG. 4 shows a cross-sectional view of a portion of the absorbent undergarment.

FIG. 4 shows a cross-sectional view of the crotch region of the absorbent undergarment 1. The absorbent undergarment according to the present disclosure comprises an absorbent structure, the absorbent pad 10, arranged on the interior surface 8 of the fabric layer 2 and covering a least part of the crotch region 7. The absorbent pad 10 may comprise 1 or more absorbent layers 11. In FIG. 4, only 1 absorbent layer is shown to increase clarity of the figure. Further, the absorbent pad 10 comprises a liquid-impermeable barrier 12 located between the one or more absorbent layers 11 and the fabric layer 2. The liquid-impermeable barrier layer 12 prevents liquid from leaking through the one or more absorbent layers 11 into the fabric layer 2. The absorbent pad further comprises a soft skin-facing layer 15 facing the skin-side of the user. The different layers of the absorbent pad 10, but additionally also the fabric layer 2, are bonded together via the leg opening seam 13.

Figure 5:
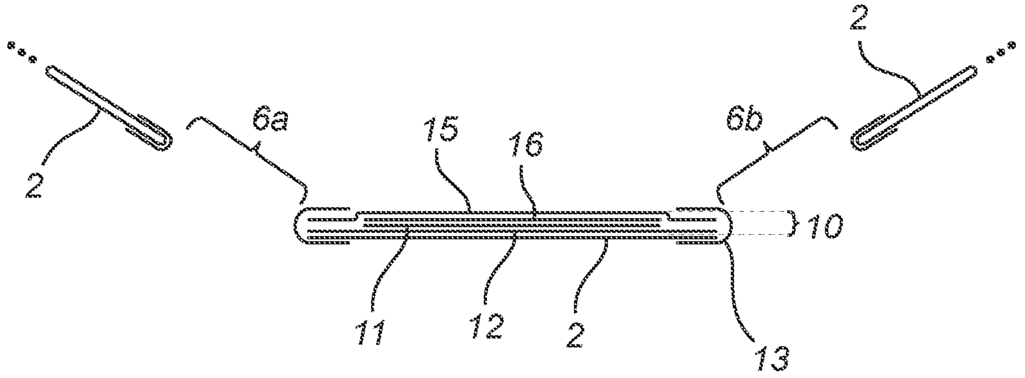
FIG. 5 shows a cross-sectional view of a portion of the absorbent undergarment according to an alternative embodiment.

FIG. 5 shows an alternative embodiment of the absorbent undergarment according to this disclosure wherein the absorbent pad further comprises a wicking layer 16 underneath the skin-facing layer 15.

The skin-facing layer 15 comprises a water-permeable material thus allowing the body fluids to migrate to the underlying absorbent layer or layers. A skin-facing layer having an open structure may further reduce the wetting zone leading to a prolonged skin beneficial effect when used in an absorbent undergarment in accordance with the present disclosure. The skin-facing layer 15 may be constructed of any suitable fabric, including naturally-derived fibers selected from the group consisting of cotton, wool, silk, cellulose, regenerated cellulose, rayon, viscose, modal, lyocell, tencel, bamboo, hemp, flax, ramie, coir or banana. Alternatively, the skin-facing layer 15 may be constructed of synthetic fibers selected from the group consisting of nylon, acrylic, polyester or elastane. Further, the skin-facing layer 15 may be constructed of a blend or a mixture of naturally-derived and/or synthetic fibers. The materials used for construction of the skin-facing layer 15 should be soft and non-irritating to the skin and be readily penetrated by body fluid, such as urine or menstrual fluid. According to the present disclosure, the skin-facing layer 15 should be launderable. When said polycarboxylic acid is provided to the skin-facing layer, the skin-facing layer comprises naturally-derived fibers comprising a free hydroxyl group to enable chemical bonding of the polycarboxylic acid to the skin-facing layer. Thus, the skin-facing layer may comprise between 20% and 100% naturally-derived fibers, more preferably between 40% and 100% naturally-derived fibers and most preferably between 60% and 100% naturally-derived fibers.

The skin-facing layer 15 may have wicking features to allow the moisture to spread away from the wearer and into the absorbent layer or layers. Further, wicking enables an efficient spread of the moisture therefore allowing the moisture to be received in a wider area of the underlying one or more absorbent layers 11. This feature is particularly relevant for users suffering from stress incontinence as spurts of urine may cause the absorbent layer to be saturated rapidly at the point of impact. By spreading the volume of the fluid over a wider receiving area in the absorbent layer, the wicking features of the skin-facing layer 15 increase the overall absorptive capacity of the absorbent layer 11. As shown in FIG. 5, a separate wicking layer 16 may be provided underneath the skin-facing layer 15.

The wicking layer 16 may comprise a water-permeable material thus allowing the body fluids to migrate to the underlying absorbent layer or layers. The wicking layer 16 may be constructed of any suitable fabric, including naturally-derived fibers selected from the group consisting of cotton, wool, silk, cellulose, regenerated cellulose, rayon, viscose, modal, lyocell, tencel, bamboo, hemp, flax, ramie, coir or banana. Alternatively, the wicking layer 16 may be constructed of synthetic fibers selected from the group consisting of nylon, acrylic, polyester or elastane. Further, the wicking layer 16 may be constructed of a blend or a mixture of naturally-derived and/or synthetic fibers. According to the present disclosure, the wicking layer 16 should be launderable. When said polycarboxylic acid is provided to the wicking layer, the wicking layer comprises naturally-derived fibers comprising a free hydroxyl group to enable chemical bonding of the polycarboxylic acid to the wicking layer. Thus, the wicking layer may comprise between 20% and 100% naturally-derived fibers, more preferably between 40% and 100% naturally-derived fibers and most preferably between 60% and 100% naturally-derived fibers.

The absorbent pad 10 for use in an absorbent undergarment may contain one or multiple absorbent layers 11, capable of absorbing liquid and releasing the liquid during laundering. Release of the absorbed liquid may be beneficial as it enables the absorbent undergarment to be restored for reuse. Reusable absorbent undergarments provide a more sustainable alternative to the commonly-used disposable hygiene articles that are not intended to be re-used.

The absorbent layer 11 may comprise any material capable of absorbing fluid, such as woven or nonwoven microfiber or polymer knits, fabric formed from hydrophilic fibers, absorbent fibers or powders. Alternatively, the absorbent layer may comprise a material treated with a hydrophilic treatment. The absorbent layer may also comprise a material having an open cell porous structures such as high loft or synthetic fibers having reservoir properties. When said polycarboxylic acid is provided to the absorbent layer, the absorbent layer comprises naturally-derived fibers comprising a free hydroxyl group to enable chemical bonding of the polycarboxylic acid to the absorbent layer. Thus, the absorbent layer may comprise between 20% and 100% naturally-derived fibers, more preferably between 40% and 100% naturally-derived fibers and most preferably between 60% and 100% naturally-derived fibers.

The liquid-impermeable barrier layer 12 may comprise any suitable material or combinations of material that prevents liquid from migrating from the absorbent pad to the fabric layer. The liquid-impermeable barrier layer 12 may comprise a hydrophobic woven or nonwoven material having inherent hydrophobic properties, or that has been treated to become hydrophobic. Examples of hydrophobic materials for treating the barrier layer are polymers such as silicone, polyurethane and combinations thereof. The liquid-impermeable barrier layer 12 may comprise a microporous polymer film, e.g. a polyethylene, PTFE or polyurethane film, or combinations thereof. Laminates of polymer films and nonwoven materials may also be used. The liquid-impermeable barrier layer 12 may comprise a moisture-impermeable polymer layer such as urethane wax on the surface facing away from the wearer.

The liquid-impermeable barrier layer 12 is preferably breathable, to allow vapor to escape from the absorbent undergarment, while preventing liquid from passing through the fabric layer. Further, the liquid-impermeable barrier layer 12 may be constructed of an elastic material, thus providing the absorbent pad 10 with the required flexibility to adapt to the user's anatomy and movements. This improved fit increases the wearer's comfort during use and helps to prevent leakage from migrating through the undergarment's leg openings.

The fabric layer 2 may be constructed of any suitable fabric, including naturally-derived fibers selected from the group consisting of cotton, wool, silk, cellulose, regenerated cellulose, rayon, viscose, modal, lyocell, tencel, bamboo, hemp, flax, ramie, coir or banana. Alternatively, the fabric layer 2 may be constructed of synthetic fibers selected from the group consisting of nylon, acrylic, polyester or elastane. Further, the fabric layer 2 may be constructed of a blend or a mixture of naturally-derived and/or synthetic fibers. The fabric layer may comprise a stretchable fabric, e.g. spandex, so that the absorbent undergarment can provide a firm fit while at the same time adapting to the wearer's movements thus preventing any leakage from migrating through the leg openings and keeping the absorbent pad in place. The fabric layer 2 is preferably breathable to allow vapor to escape from the wearer's skin and from the absorbent structure. The fabric layer 2 may be constructed of the same material as the skin-facing layer to give the absorbent underwear a more uniform appearance and to make the absorbent pad more discrete.

The skin-facing layer 15, the absorbent pad 10, the fabric layer 2 and the optionally present wicking layer 16 may be bonded by conventional stitching, gluing techniques or via a bonding film such as tape.

According to the present disclosure, it is beneficial to provide the absorbent undergarment with an acidic pH that will be maintained after laundering the absorbent undergarment, i.e. a permanent acidification. The acidic pH reduces microbial growth thus increasing the hygienic properties of the absorbent undergarment while at the same time preventing unwanted odors caused by microbial metabolites. This is achieved by providing a polycarboxylic acid to the absorbent undergarment. Polycarboxylic acids are organic and biodegradable and therefore have a limited environmental impact.

The permanent acidification may be achieved by providing an acidic treatment comprising a polycarboxylic acid comprising two to ten carboxyl groups. A first carboxyl group is required to allow binding of the polycarboxylic acid to the material constituting the absorbent undergarment, whereas the additional carboxyl groups provide the acidic properties. The polycarboxylic acid binds through the formation of an esterbond with a free hydroxyl group in the material of the absorbent article. In this respect, it is essential that the material to which the acidic solution is to be applied, comprises naturally-derived fibers as these fibers contain a free hydroxyl group.

The polycarboxylic acid may comprise at least three carboxyl groups, such as citric acid. After binding of the carboxyl group to the fibers in the absorbent undergarment, two carboxyl groups remain to provide the absorbent undergarment with the desired acidic pH. The presence of several remaining carboxyl groups after binding, results in a further lowering of the pH of the absorbent undergarment.

The acidic solution may comprise between 2 and 80% polycarboxylic acid, more preferably between 5 and 50% polycarboxylic acid and most preferably between 10 and 30% polycarboxylic acid. The acidic solution may be applied to a layer selected from the absorbent layer, the skin-facing layer, and/or optionally present wicking layer, or several selected layers, for a time period between 20 seconds to 30 minutes, more preferably between 30 second and 15 minutes and most preferably between 30 seconds and 5 minutes. A subsequent curing step enables the carboxyl-group of the polycarboxylic acid to bond with the hydroxyl group in the naturally-derived fiber. The treatment solution may comprise a catalyst to accelerate the process.

The acidic solution may be essentially homogenously applied to a layer selected from the absorbent layer, the skin-facing layer, and/or optionally present wicking layer. The acidic solution may be applied in a patterned manner, covering only part of the surface of the layer on which it is applied. It is contemplated that in one and the same product, the acidic solution may be homogenously applied to one selected layer, and furthermore applied in a patterned manner on another selected layer.

The present disclosure further pertains to a method for manufacturing an absorbent undergarment as disclosed in the above paragraphs. The method comprises the steps of disposing an absorbent pad comprising at least one absorbent layer and a skin facing layer, on a fabric layer. Next, the naturally-derived fibers are treated with a treatment solution comprising one or more polycarboxylic acids or salts thereof, preferably a polycarboxylic acid as defined in the present disclosure. Optionally, a drying step may be included. Finally, a curing step is required to obtain the absorbent undergarment. At least one and preferably all of the following conditions may be fulfilled in the method for manufacturing the absorbent undergarment.

(i) the concentration of the polycarboxylic acid in the treatment solution is 2 to 80 wt.-%, preferably 2.5 to 50 wt.-% and more preferably 10 to 20% wt.-% based on the total weight of the treatment solution, (ii) the treatment time is 20 sec to 30 min, preferably 30 sec to 15 min, in particular 30 sec to 5 min, (iii) the curing time is 10 sec to 10 min, preferably 10 sec to 1 min, in particular 10 sec to 30 sec, (iv) the curing temperature is 100° C. to 200° C., preferably 110° C. to 180° C., more preferably 140° C. to 170° C.

The treatment solution may comprise a catalyst. The catalyst may be selected from the group consisting of sodium hypophosphite, disodium monohydrogen phosphate, sodium dihydrogen phosphate, sodium salt of maleic acid or sodium pyrophosphate.

The selected layer of the absorbent undergarment according to the present disclosure may have a pH after one washing cycle of from 2.5 to 6.5 when measured according to the method described herein. The selected layer of the absorbent undergarment according to the present disclosure may have a pH after 5 washing cycles of from 2.5 to 6.5 when measured according to the method described herein.

Benefits of absorbent undergarments in accordance with the present disclosure will now be described with reference to the following non-limiting examples.

Example 1: Antibacterial Effect

In this example the antibacterial effect of polycarboxylic acid bonded to naturally-derived fibers in cotton and bamboo viscose fabric samples was tested. It was shown that with the presence of citric acid reduces the growth of the tested bacteria.

Test Method for Measuring Bacterial Growth

The antibacterial effect was measured using the standard method AATC100 "Assessment of Antibacterial Finishes on Textile Materials".

Briefly, bacterial strains *Escherichia coli* (ATCC 1175), *Enterococcus faecalis* (P120 Clinical Isolate) and *Staphylococcus epidermidis* (P136 Clinical Isolate) were diluted in 100% Tryptic Soy Broth (TSB) to obtain a start concentration of log 5 colony-forming units per milliliter ($10^5$ CFU/ml). Alternatively, a different strain from the species *Escherichia coli, Enterococcus faecalis* or *Staphylococcus epidermidis* may be used in this test method. Test materials were inoculated with 1 ml of respective bacterial cultures and incubated at 35° C. for 6 hours. Bacteria were released from the fabric by running the samples for 1 minute at high speed using Letheen Broth in a Stomacher paddle blender (Stomacher 400, Seward). The bacteria were plated on Tryptic Soy Agar (TSA) and incubated for 20 h at 35° C. until colonies were countable.

Bacterial growth was measured as colony-forming units per milliliter (CFU/ml) by plate counting. Number of bacteria were compared to both initial numbers and to the reference material.

Materials Used

The following fabric samples were tested: a knitted two-thread fleece fabric consisting of 100% cotton and a knitted two-thread fleece fabric consisting of 70% bamboo viscose and 30% cotton. The samples were fully emerged in a lukewarm aqueous solution containing 10% Citric Acid, available from Fisher Scientific, and 5% Sodium Hypophosphite, available from Fisher Scientific, for 5 minutes. After removing the excess water, the fabric samples were cured for 10 minutes at 160 degrees Celsius and rinsed in lukewarm water. Next, the fabric samples were machine-washed (WKG130 NDS TDos, Miele) at 60 degrees Celsius using pre-programmed settings optimized for cotton washing in the presence of 50 ml of a two-component liquid washing detergent (UltraPhase I &II, Miele). As a reference material, the same fabric material was used without any kind of treatment.

Results

Figure 2:
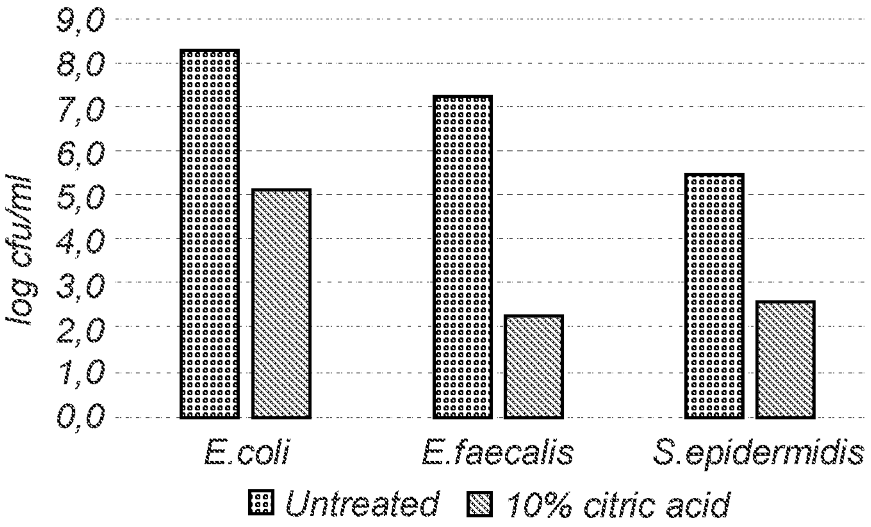
FIG. 2 shows a graph depicting bacterial growth on fabric consisting of a bamboo viscose/cotton blend.

Results from the bacterial growth measurements on the knitted two-thread fleece fabric consisting of 100% cotton are shown in FIG. 1. Results from the bacterial growth measurement on the knitted two-thread fleece fabric consisting of 70% bamboo viscose and 30% cotton are shown in FIG. 2.

From these results, it is clear that treatment with Citric Acid reduces bacterial growth on cotton and bamboo viscose fabric samples.

Example 2: pH Stability

In this example pH was measured on treated cotton and bamboo viscose fabric samples after washing. Fabric samples treated with a Citric Acid-solution were compared to untreated samples. It was shown that the treatment with Citric Acid confers a low pH to the fabric sample that remains low after washing.

Test Method for Measuring pH of Fabric Sample

The pH of the surface of the fabric sample was measured using a pH meter (PH-METER, VWR™ SYMPHONY, SB 80PI and the pH electrode used was HAMILTON 10 FLATRODE).

The treated fabric was rinsed in tap water and wringed out. The pH meter rod was rinsed with deionized water and dipped in 0.9% NaCl solution. A small droplet of saline solution was hanging from the electrode and wetted the fabric sample at the point of measurement. All the pH measurements were performed at 23° C. and approx.50% RH.

Materials Used

The following fabric samples were tested: a knitted two-thread fleece fabric consisting of 100% cotton, a knitted two-thread fleece fabric consisting of 70% bamboo viscose and 30% cotton and a knitted two-thread fleece fabric consisting of a 55% hemp/45% cotton blend. The samples were fully emerged in a lukewarm aqueous solution containing 10% Citric Acid, available from Fisher Scientific, and 5% Sodium Hypophosphite, available from Fisher Scientific, for 5 minutes. After removing the excess water, the fabric samples were cured for 10 minutes at 160 degrees Celsius and rinsed in lukewarm water. Next, the fabric samples were machine-washed (WKG130 NDS TDos, Miele) at 60 degrees Celsius using pre-programmed settings optimized for cotton washing in the presence of 50 ml of a two-component liquid washing detergent (UltraPhase I &II, Miele). As a reference material, the same fabric material was used without any kind of treatment.

Results

Results from the pH measurements are shown below in table 1. Results shown pH measurement after washing of the fabric samples as described above.

| Fabric Sample | pH untreated reference | pH treated sample |
|---|---|---|
| 100% Cotton | 7.2 | 5.6 |
| 70% Bamboo Viscose | 7.0 | 5.2 |
| 55% Hemp 45% Cotton | 7.2 | 5.7 |

From the results above, it is clear that a treatment with citric acid of fabric samples maintains a lower pH after washing as compared to untreated fabric samples.

Example 3: Effect of Curing Step and Catalyst

In this example, fabric samples were treated with a Citric Acid-solution in the presence or absence of a catalyst and with and without curing. It was shown that the treatment with Citric Acid in the presence of a catalyst and with a curing step confers a low pH to the fabric sample that remains low after washing.

Test Method for Measuring pH of Fabric Sample

The pH of the surface of the fabric sample was measured using a pH meter (PH-METER, VWR™ SYMPHONY, SB 80P1 and the pH electrode used was HAMILTON 10 FLATRODE).

The treated fabric was rinsed in tap water, wringed out and followed by dipping in 0.9% NaCl solution before being wringed out again for the pH measurement. The pH meter rod was rinsed with deionized water and dipped in 0.9% NaCl solution and then placed on the fabric sample for measurement. A small droplet of saline solution was hanging from the electrode and wetted the fabric sample at the point of measurement. All the pH measurements were performed at 23° C. and approx.50% RH.

Materials and Treatments

In this test cotton fabric samples (100% cotton) were subjected to different treatment conditions according to table 2. The samples were treated with citric acid with or without temperature curing and with and without catalyst. Sodium hypophosphite was used as a catalyst in sample 4 and 6, whereas di-sodium hydrogen phosphate was used as a catalyst in sample 5 and 7. As a reference, the same fabric material was used without any kind of treatment (sample 1). The samples 2 to 7 were fully emerged in an aqueous solution for 5 minutes containing 20% Citric Acid. In the catalyst treated samples the solution also contained 10% Sodium Hypophosphite or 18% di-sodium hydrogen phosphate (both catalysts hence in the same molar concentration). All chemicals used are available from Fisher Scientific. After treatment the excess solution was removed by wringing and left to dry in room temperature or cured for 5 minutes at 155 degrees Celsius.

All samples were laundred in a household washing machine (WKG130 NDS TDos, Miele) at 40 degrees Celsius using pre-programmed settings with standard detergent (Grumme flytande kulör, by Orkla Care).

Results

Results from the pH measurements are shown below in table 2. Results show pH measurement after washing of the fabric samples as described above.

| | Curing | Catalyst Added | Resulting pH |
|---|---|---|---|
| Sample 1 = reference | No | No | 6.4 |
| Sample 2 | No | No | 6.4 |
| Sample 3 | Yes | No | 5.7 |
| Sample 4 | Yes | Yes | 4.6 |
| Sample 5 | Yes | Yes | 5.4 |
| Sample 6 | No | Yes | 6.3 |
| Sample 7 | No | Yes | 6.5 |

From the results above, it is clear that a treatment with citric acid of fabric samples in the presence of a catalyst and with an additional curing step has a lower pH after washing as compared to fabric samples treated with citric acid in the absence of a catalyst and curing step.

The invention claimed is:

1. An absorbent undergarment comprising a fabric layer defining a waist opening, two leg openings and a crotch region between the leg openings, said absorbent undergarment further comprising an absorbent pad covering at least a part of said crotch region and being permanently attached to the fabric layer, said absorbent pad comprising at least one absorbent layer and a skin-facing layer,
   wherein at least one layer, selected from said absorbent layer, said skin-facing layer or an optionally present wicking layer, comprises naturally-derived fibers comprising a polycarboxylic acid,
   wherein the polycarboxylic acid has at least three carboxyl groups including at least one carboxyl group covalently bound to the naturally-derived fibers and at least two free carboxyl groups, and
   wherein said at least one layer comprising naturally-derived fibers has a pH after one washing cycle of from 2.5 to 5.2.

2. The absorbent undergarment according to claim 1, wherein the polycarboxylic acid has three to ten carboxyl groups.

3. The absorbent undergarment according to claim 1, wherein the polycarboxylic acid has 2 to 12 carbon atoms in a main chain.

4. The absorbent undergarment according to claim 1, wherein at least one carboxyl group is covalently bound to the naturally-derived fibers by forming an ester group with a hydroxy group present in the naturally-derived fiber.

5. The absorbent undergarment according to claim 1, wherein said at least one layer comprises between 20% and 100% naturally-derived fibers.

6. The absorbent undergarment according to claim 1, wherein said at least one layer comprises between 40% and 100% naturally-derived fibers.

7. The absorbent undergarment according to claim 1, wherein said at least one layer comprises between 60% and 100% naturally-derived fibers.

8. The absorbent undergarment according to claim 1, wherein said naturally-derived fibers are selected from the group consisting of natural fibers and man-made regenerated fibers from a natural source.

9. The absorbent undergarment according to claim 8, wherein said naturally-derived fibers are selected from the group consisting of cotton, wool, silk, cellulose, regenerated cellulose, rayon, viscose, modal, lyocell, tencel, bamboo, hemp, flax, ramie, coir or banana.

10. The absorbent undergarment according to claim 9, wherein said naturally-derived fibers are selected from the group consisting of cotton or viscose fibers.

11. The absorbent undergarment according to claim 1, wherein said at least one layer comprising naturally-derived fibers is substantially free of petroleum-based materials.

12. The absorbent undergarment according to claim 1, wherein the naturally-derived fibers comprising a polycarboxylic acid are obtainable by treating the naturally-derived fibers with a polycarboxylic acid, followed by a curing step.

13. The absorbent undergarment according to claim 12, wherein the treatment of the naturally-derived fibers with a polycarboxylic acid, occurs in the presence of a catalyst.

14. Method for producing an absorbent undergarment comprising an absorbent pad comprising at least one absorbent layer and a skin-facing layer and optionally a wicking layer, comprising the steps of:
   (i) treating naturally-derived fibers with a treatment solution comprising one or more polycarboxylic acid, or optionally a mixture of one or more polycarboxylic acids or salts thereof;
   (ii) optionally drying;
   (iii) curing; and
   (iv) incorporating the treated fibers in at least one layer of the absorbent undergarment, selected from said absorbent layer, said skin-facing layer and said wicking layer, if present,
   wherein the one or more polycarboxylic acid has at least three carboxyl groups including at least one carboxyl group covalently bound to the naturally-derived fibers and at least two free carboxyl groups, and
   wherein said at least one layer comprising treated fibers has a pH after one washing cycle of from 2.5 to 5.2.

15. The method according to claim 14, wherein at least one of the following conditions is fulfilled:
   the concentration of the polycarboxylic acid in the treatment solution is 2 to 80 wt.-% based on the total weight of the treatment solution,
   the treatment time is 20 sec to 30 min, the curing time is 10 sec to 10 min, and
the curing temperature is 100° C. to 200° C.

16. The method according to claim 14, wherein the treatment solution comprises a catalyst.

17. The method according to claim 14, wherein the absorbent undergarment comprises a fabric layer defining a waist opening, two leg openings and a crotch region between the leg openings and wherein the absorbent pad is permanently attached to the fabric layer.

18. The absorbent undergarment according to claim 13, wherein the catalyst is selected from the group consisting of sodium hypophosphite, disodium monohydrogen phosphate, sodium dihydrogen phosphate, sodium salt of maleic acid or sodium pyrophosphate.

19. Method for producing an absorbent undergarment comprising an absorbent pad comprising at least one absorbent layer and a skin-facing layer and optionally a wicking layer, comprising the steps of:

(i) treating naturally-derived fibers with a treatment solution comprising one or more polycarboxylic acid, or optionally a mixture of one or more polycarboxylic acids or salts thereof, wherein a treatment time is 20 seconds to 30 minutes;

(ii) optionally drying;

(iii) curing for 10 seconds to 10 minutes; and (iv) incorporating the treated fibers in at least one layer of the absorbent undergarment, selected from said absorbent layer, said skin-facing layer and said wicking layer, if present, wherein the one or more polycarboxylic acid has at least three carboxyl groups including at least one carboxyl group covalently bound to the naturally-derived fibers and at least two free carboxyl groups, and wherein said at least one layer comprising treated fibers has a pH after one washing cycle of from 2.5 to 5.2.

20. The absorbent undergarment according to claim 1, wherein said at least one layer comprising naturally-derived fibers has a pH after 5 washing cycles of from 2.5 to 6.5.

21. The absorbent undergarment according to claim 1, wherein the polycarboxylic acid is selected from the group consisting of citric acid, isocitric acid, citraconic acid, tartaric acid, itaconic acid, 1,2,3-propanetricarboxylic acid, 1,2,3,4-butanetetracarboxylic acid, glutaric acid, alpha-ketoglutaric acid, malic acid, malonic acid, 2-hydroxymalonic acid, oxalic acid, oxalosuccinic acid, succinic acid, carboxy succinic acid, 1,2 dimethylsuccinic acid, adipic acid, pimelic acid, 2-methyl tricarballylic acid, aconitic acid, 1,2,4-butane tricarboxylic acid, polymers of acrylic acid, and mixtures thereof.

* * * * *